(12) United States Patent
Abdollahi et al.

(10) Patent No.: US 7,142,707 B2
(45) Date of Patent: Nov. 28, 2006

(54) AUTOMATED INSPECTION OF PACKAGING MATERIALS FOR PACKAGE INTEGRITY

(75) Inventors: Mohsen Abdollahi, Huntsville, AL (US); Kevin H. Giles, Knoxville, TN (US); Charles L. Guffey, Sweetwater, TN (US); Jun Liu, Knoxville, TN (US); Bernard Roche, Farragut, TN (US); Peter W. Sites, Knoxville, TN (US); Robert P. Whalen, Knoxville, TN (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 10/734,358

(22) Filed: Dec. 12, 2003
(Under 37 CFR 1.47)

(65) Prior Publication Data

US 2005/0050451 A1   Mar. 3, 2005

(51) Int. Cl.
*G06K 9/00* (2006.01)
(52) U.S. Cl. ...................... 382/143; 382/142; 382/108; 382/110
(58) Field of Classification Search ................ 382/110, 382/108, 141–143; 356/451, 319, 302, 237, 356/239; 348/86, 127, 125–131
See application file for complete search history.

(56) References Cited

U.S. PATENT DOCUMENTS 4,747,299 A   5/1988   Fox et al.
5,515,159 A   5/1996   Sites et al.
5,805,279 A * 9/1998   Palombo et al. ......... 356/239.4
5,926,268 A * 7/1999   Bonewitz et al. ........ 356/240.1
6,301,380 B1  10/2001  Mullins et al.
2003/0044056 A1* 3/2003  Katt et al. ................... 382/143
2003/0161524 A1* 8/2003  King .......................... 382/141

FOREIGN PATENT DOCUMENTS

EP        06/85731        12/1995

OTHER PUBLICATIONS

Wikipedia Foundation, Visible Spectrum, encyclopedia, Jul. 11, 2006, 3 pgs.,http://en.wikipedia.org/wiki/Visible_spectrum, United States.
Wikipedia Foundation, Fluorescence, encyclopedia, Jul. 7, 2006, 5 pgs.,http://en.wikipedia.org/wiki/Fluorescence, United States.
Siemens AG 2006, Cloudy Day Illuminator, catalog, 2006, 1 pg., http://www.nerlite.com/CDI.html, United States.

* cited by examiner

*Primary Examiner*—Samir Ahmed
*Assistant Examiner*—Wes Tucker
(74) *Attorney, Agent, or Firm*—Carmen B. Patti & Assoc. LLC

(57) ABSTRACT

An apparatus in one example comprises a computer component that receives one or more images of one or more packaging materials from one or more imaging components. The computer component employs an analysis of the one or more images to make a determination of a package integrity of the one or more packaging materials.

19 Claims, 4 Drawing Sheets

AUTOMATED INSPECTION OF PACKAGING MATERIALS FOR PACKAGE INTEGRITY

TECHNICAL FIELD

The invention relates generally to computer systems and more particularly to analysis of packaging materials by computer systems.

BACKGROUND

Most types of consumer and commercial products are placed in some type of packaging material. The packaging material is responsible for product protection and preservation. The packaging materials in one example comprise one or more seal regions. For example, the seal regions are responsible for keeping one or more of a food product, a pharmaceutical, a medical device, and a cosmetic safe, fresh, and/or pathogen free.

Currently, manufacturers and/or processors employ one or more techniques to ensure package integrity of the packaging materials. In one example, the techniques comprise offline statistical testing on the packaging materials. For example, the manufacturers puncture and/or pressurize the packaging materials to test package integrity. In another example, the techniques comprise employment of water baths to identify leaks in the packaging materials. In yet another example, the techniques comprise employment of one or more users to manually inspect the packaging materials.

One or more shortcomings exist for package integrity testing of the packaging materials. As one shortcoming of one or more of the techniques, 100% of the packaging materials cannot be tested. As another shortcoming, one or more of the technique destroys normal packaging materials and one or more products of the packaging materials. As yet another shortcoming, one or more of the techniques are cost prohibitive. One or more of the shortcomings exist due to widely varying packaging types, widely varying product types, large numbers of defects per packaging/product type, and the subtle nature of the defects.

Thus, a need exists to employ a computer component to perform an analysis of packaging materials to make a determination of a package integrity.

SUMMARY

The invention in one implementation encompasses an apparatus. The apparatus comprises a computer component that receives one or more images of one or more packaging materials from one or more imaging components. The computer component employs an analysis of the one or more images to make a determination of a package integrity of the one or more packaging materials.

Another implementation of the invention encompasses a method. One or more irradiation components are employed to emit one or more radiation wavelengths to one or more packaging materials. One or more images of the one or more packaging materials are received from one or more imaging components. One or more analysis algorithms on the one or more images are employed to make a determination of a package integrity of the one or more packaging materials.

A further implementation of the invention encompasses an article. The article comprises one or more computer-readable signal-bearing media. The article comprises means in the one or more media for employing one or more irradiation components to emit one or more radiation wavelengths to one or more packaging materials. The article comprises means in the one or more media for receiving one or more images of the one or more packaging materials from one or more imaging components. The article comprises means in the one or more media for employing one or more analysis algorithms on the one or more images to make a determination of a package integrity of the one or more packaging materials.

DESCRIPTION OF THE DRAWINGS

Features of exemplary implementations of the invention will become apparent from the description, the claims, and the accompanying drawings in which:

DETAILED DESCRIPTION

Figure 1:
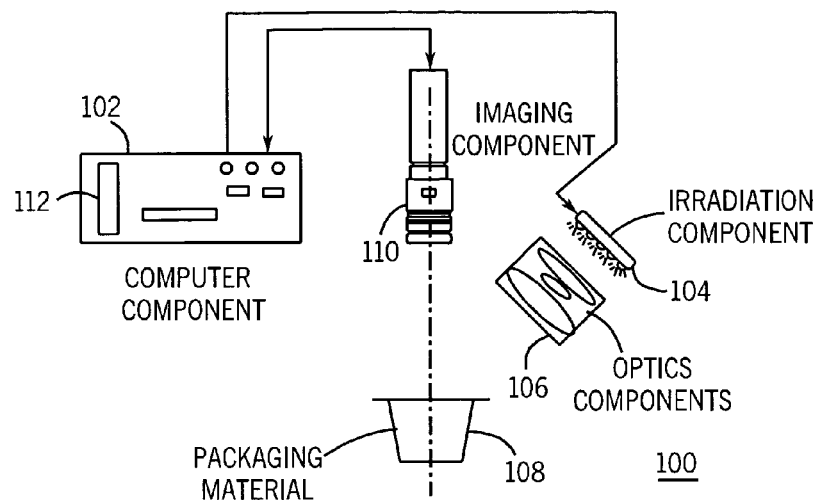
FIG. 1 is a representation of an exemplary implementation of an apparatus that comprises one or more computer components, one or more irradiation components, one or more optical components, and one or more imaging components.

Turning to FIG. 1, an apparatus 100 in one example comprises a plurality of components such as computer software and/or hardware components. A number of such components can be combined or divided in the apparatus 100. An exemplary component of the apparatus 100 employs and/or comprises a set and/or series of computer instructions written in or implemented with any of a number of programming languages, as will be appreciated by those skilled in the art.

The apparatus 100 in one example comprises one or more computer components 102, one or more irradiation components 104, one or more optical components 106, and one or more imaging components 110. The computer component 102 in one example employs the irradiation component 104 to emit one or more radiation wavelengths through the optical component 106. Upon the radiation wavelengths striking one or more packaging materials 108, the imaging component 110 creates one or more images of the packaging material 108. The computer component 102 receives the images from the imaging component 110. For example, the computer component 102 employs an analysis of the images to determine a package integrity of the packaging material 108.

The computer component 102 in one example communicates with the irradiation component 104 and the imaging component 110. The computer component 102 sends one or more signals to initiate one or more of the irradiation component 104 and the imaging component 110. In one example, the computer component 102 initiates the irradiation component 104 to emit one or more radiation wavelengths to the packaging material 108. In another example, the computer component 102 initiates the imaging component 110 to create one or more images of the packaging material 108. Upon creation of the images, the imaging component 110 sends the images to the computer component 102.

The computer component 102 comprises an instance of the data recordable storage medium 112. The computer component 102 in one example employs one or more algorithms to determine a package integrity. For example, the algorithms are based on one or more of the irradiation component 104, the radiation wavelength, the optical component 106, the packaging material 108, and the image. In one example, the package integrity is normal. In another example, the package integrity is defective. For example, a defective packaging material may contain one or more channel leaks, entrapped particles, tears, and/or punctures. The computer component 102 in one example is able to automatically inspect the package integrity of the packaging materials 108 through the employment of the irradiation components 104 and the imaging components 110.

The irradiation component 104 in one example emits one or more radiation wavelengths to the packaging material 108. For example, the irradiation component 104 emits the radiation wavelengths at an angle of incidence to the packaging material 108. In one example, the irradiation component 104 comprises a front lighting arrangement. In another example, the irradiation component 104 comprises a back lighting arrangement. The irradiation component 104 comprises one or more of a visible light source, an infrared source, and an ultraviolet source. The radiation wavelengths may be structured, semi-structured, or diffuse. The radiation wavelengths in one example allow the imaging component 110 to create an image of the packaging material 108. The radiation wavelengths comprise one or more of a visible light wavelength, an infrared wavelength, and an ultraviolet wavelength.

The radiation wavelengths in one example pass through the optical components 106. The optical components 106 comprise one or more of a lens, a grating, a low-pass filter, a band-pass filter, and a high-pass filter. In one example, the optical components 106 filter out one or more wavelengths of the radiation wavelengths. In another example, the optical components 106 alter the angle of incidence of one or more wavelengths of the radiation wavelengths.

The packaging material 108 in one example transmits or reflects one or more portions of the radiation wavelengths to the imaging component 110. In one example, the packaging material 108 comprises one or more of a translucent, a semi-translucent, a transparent, a semi-transparent, and an opaque material. For example, the packaging material 108 allows a transmittance of one or more radiation wavelengths. In another example, the packaging material 108 comprises one or more of a specular or semi-specular material. For example, the packaging material 108 allows a reflectance of one or more radiation wavelengths.

The packaging material 108 in one example contains food products. For example, the packaging material 108 comprises a pouch, a lid stock, a bowl, a paperboard container, and a cup. The packaging material 108 comprises one or more of a flexible, a semi-rigid, and a rigid material. In one example, the packaging material 108 comprises one or more seal regions. In another example, the packaging material 108 comprises one or more flanges, i.e. unclosed seal regions. In yet another example, the packaging material 108 comprises graphics and/or text.

The imaging component 110 in one example creates one or more images of the packaging material 108. For example, the imaging component 110 employs one or more radiation wavelengths to create the images. In one example, the computer component 102 initiates the imaging component 110 to create the images. In another example, the computer component 102 receives the images from the imaging component 110. The computer component 102 employs an analysis of the images to determine a package integrity of the packaging material 108. The imaging component 110 in one example comprises one or more of a digital camera, a video camera, and a magnifier.

Figure 2:
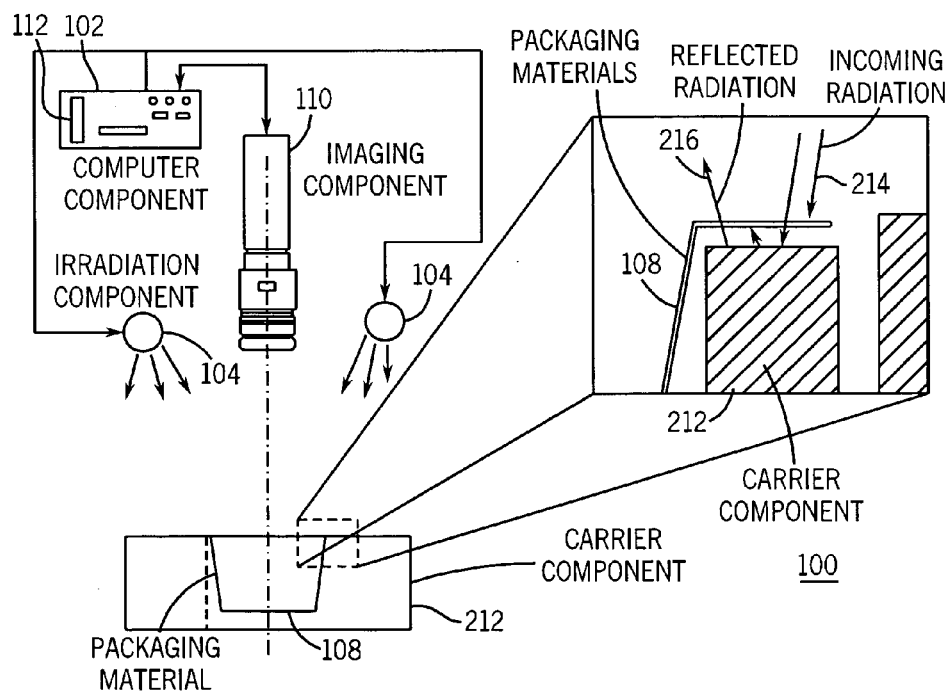
FIG. 2 is a representation of an exemplary implementation of one or more radiation wavelengths illustrating an employment of a carrier of the packaging material that reflects the radiation wavelengths from the one or more irradiation components to the imaging component of FIG. 1.

Referring to FIGS. 1 and 2, an illustrative description of exemplary operation of the apparatus 100 is now presented, for explanatory purposes. A carrier 212 of the packaging material 108 reflects one or more radiation wavelengths from the one or more irradiation components 104 to the imaging component 110. For example, the imaging component 110 employs one or more radiation wavelengths 216 to create one or more images of the packaging material 108.

The computer component 102 initiates the irradiation components 104. The irradiation components 104 in one example comprise one or more front lighting arrangements. The irradiation components 104 in one example emit one or more radiation wavelengths 214 toward the packaging material 108. The radiation wavelengths 214 in one example comprise structured, semi-structured, or diffuse radiation wavelengths. The packaging material 108 in one example comprises one or more translucent or semi-translucent materials with one or more flanges or seals. The packaging material 108 comprises one or more of a cup, a tray, and a tub that sit on the carrier 212.

The carrier 212 in one example is reflective. The packaging material 108 in one example allows a transmittance of one or more of the radiation wavelengths 214. The radiation wavelengths 214 transmit through the packaging material 108 and one or more of the radiation wavelengths 216 reflect off the carrier 212 toward the imaging component 110.

The computer component 102 in one example initiates the imaging component 110. For example, the imaging component 110 employs one or more of the radiation wavelengths 216 to create one or more images of the packaging material 108. Upon creation of the images, the imaging component 110 sends the images to the computer component 102. The computer component 102 in one example employs one or more analysis algorithms and the images to determine the package integrity of the packaging material 108.

Figure 3:
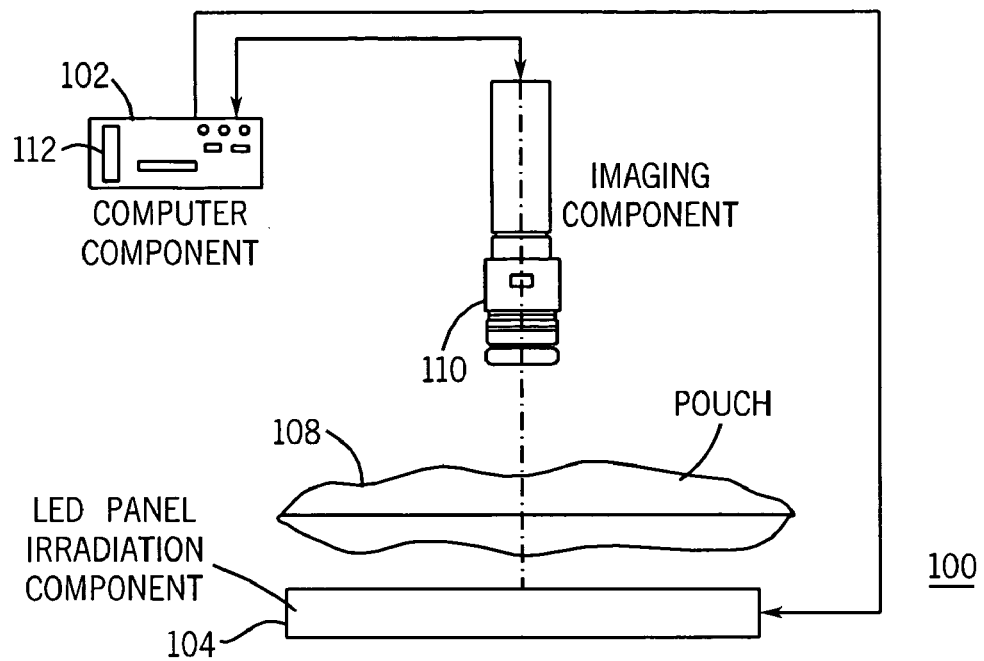
FIG. 3 is a representation of an exemplary implementation of one or more radiation wavelengths illustrating an employment of an irradiation component that emits the radiation wavelengths through the packaging material toward the imaging component of FIG. 1.

Referring to FIGS. 1 and 3, an illustrative description of exemplary operation of the apparatus 100 is now presented, for explanatory purposes. The irradiation component 104 emits one or more radiation wavelengths through the packaging material 108 toward the imaging component 110. The imaging component 110 employs the radiation wavelengths to create one or more images of the packaging material 108.

The computer component 102 initiates the irradiation component 104 to emit the radiation wavelengths. The irradiation component 104 in one example comprises an LED panel in a back lighting arrangement. The radiation wavelengths in one example comprise structured, semi-structured, or diffuse radiation wavelengths. The packaging material 108 in one example comprises one or more transparent, translucent, or semi-translucent pouches. For example, the packaging material 108 allows a transmittance of one or more of the radiation wavelengths. The irradiation component 104 emits one or more radiation wavelengths through the packaging material 108 toward the imaging component 110.

The computer component 102 in one example initiates the imaging component 110. For example, the imaging component 110 employs one or more of the radiation wavelengths to create one or more images of the packaging material 108. The imaging component 110 sends the images to the computer component 102. The computer component 102 in one example employs one or more analysis algorithms and the images to determine the package integrity of the packaging material 108. For example, the analysis algorithms may accept or reject the packaging material 108 based on one or more entrapped particles in the seal of the packaging material 108.

Figure 4:
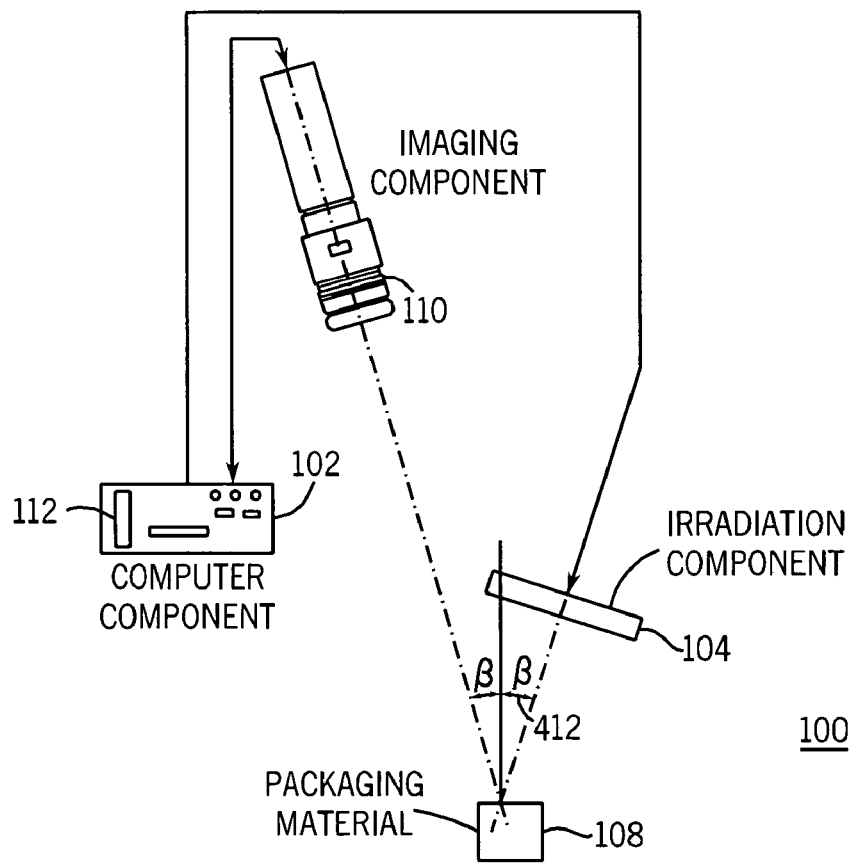
FIG. 4 is a representation of an exemplary implementation of one or more radiation wavelengths illustrating an employment of an irradiation component that emits the radiation wavelengths toward the packaging material for a reflection to the imaging component of FIG. 1.

Referring to FIGS. 1 and 4, an illustrative description of exemplary operation of the apparatus 100 is now presented, for explanatory purposes. The irradiation component 104 emits one or more radiation wavelengths toward the packaging material 108. The radiation wavelengths reflect off the packaging material 108 toward the imaging component 110. For example, the imaging component 110 employs the radiation wavelengths to create one or more images of the packaging material 108.

The computer component 102 initiates the irradiation component 104. The irradiation component 104 comprises an angled front lighting arrangement. The irradiation component 104 in one example emits one or more radiation wavelengths at an incident angle 412 toward the packaging material 108. For example, the incident angle 412 is less than 45°. The radiation wavelengths in one example comprise structured, semi-structured, or diffuse radiation wavelengths. The packaging material 108 in one example comprises one or more of a flexible material and a semi-rigid packaging material. The packaging material 108 in one example comprises a planar specular material or a planar semi-specular material. For example, the packaging material 108 in one example allows a reflectance of one or more of the radiation wavelengths toward the imaging component 110. In one example, the packaging material 108 causes the reflection of the radiation wavelengths at a reflected angle equal to the incident angle 412. In another example, the packaging material 108 causes the reflection of one or more of the radiation wavelengths at a reflected angle different from the incident angle 412.

Upon a reflection of the radiation wavelengths toward the imaging component 110, the computer component 102 initiates the imaging component 110. The imaging component 110 employs one or more of the radiation wavelengths to create one or more images of the packaging material 108. The imaging component 110 sends the images to the computer component 102.

The computer component 102 in one example employs one or more analysis algorithms and the images to determine the package integrity of the packaging material 108. In one example, where the reflected angle equals the incident angle, the analysis algorithms identify one or more bright regions in the images. The bright regions indicate a planar nature of the packaging material 108. For example, the package integrity of the packaging material is normal. In another example, where the reflected angle is different from the incident angle, the analysis algorithms identify one or more dark regions in the images. The dark regions indicate a loss in the planar nature of the packaging material 108. For example, the package integrity of the packaging material is defective. Where the packaging material 108 comprise graphics and/or text, for example in a seal region of the packaging material 108, the imaging component 110 creates one or more images for the computer component 102 that do not show the graphics and/or the text.

Figure 5:
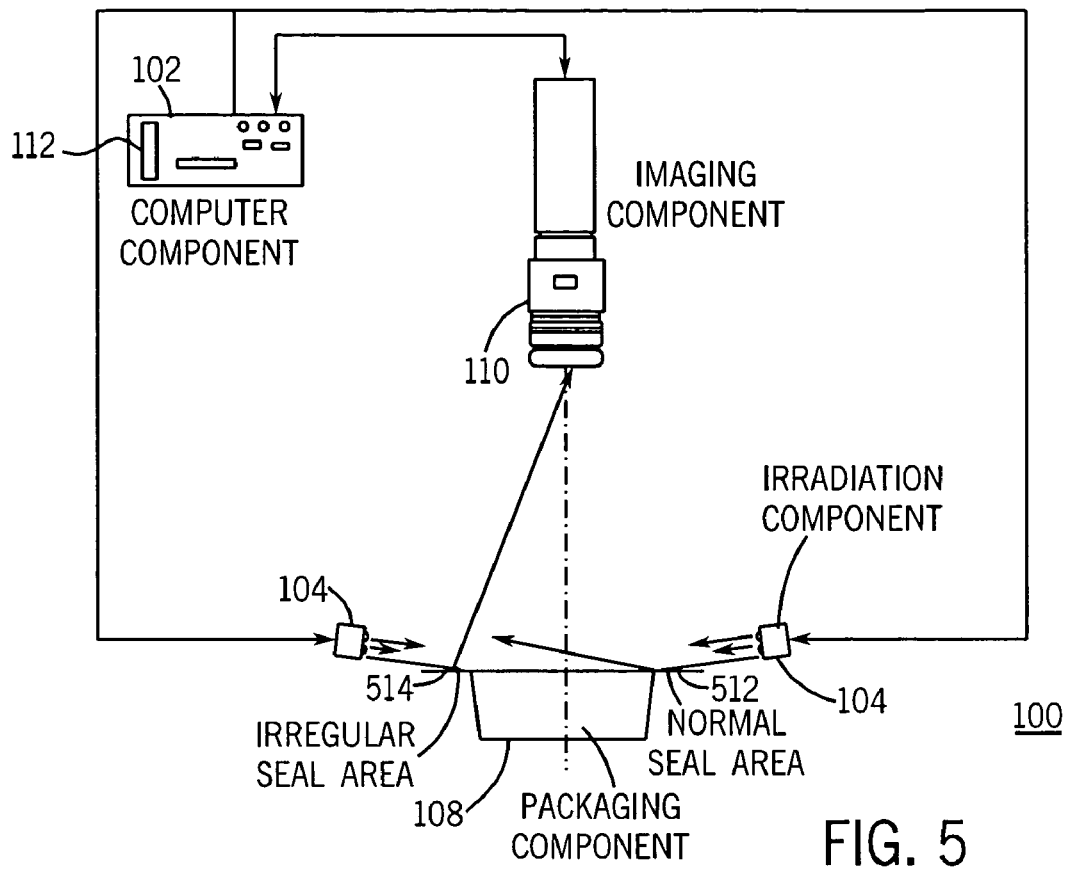
FIG. 5 is a representation of an exemplary implementation of one or more radiation wavelengths illustrating an employment of an irradiation component that emits the radiation wavelengths toward the packaging material of FIG. 1. Upon a reflection of the radiation wavelengths from the packaging material, the imaging component creates one or more images of the packaging material.

Referring to FIGS. 1 and 5, an illustrative description of exemplary operation of the apparatus 100 is now presented, for explanatory purposes. The irradiation component 104 emits one or more radiation wavelengths toward the packaging material 108. Upon a reflection of the radiation wavelengths from the packaging material 108, the imaging component 110 creates one or more images of the packaging material 108.

The computer component 102 in one example initiates the irradiation component 104. The irradiation component 104 comprises an angled front lighting arrangement. The irradiation component 104 in one example emits one or more radiation wavelengths at an incident angle greater than 45° toward the packaging material 108. The radiation wavelengths and the packaging material 108 in one example comprise one or more of the radiation wavelengths and the packaging materials as described in FIG. 4.

Upon a reflection of the radiation wavelengths from the packaging material 108, the computer component 102 initiates the imaging component 110. In one example, the packaging material 108 comprises a normal seal region 512. For example, the packaging material 108 causes one or more the radiation wavelengths to reflect away from the imaging component 110. In another example, the packaging material 108 comprises an irregular seal region 514. For example, the packaging material 108 causes one or more of the radiation wavelengths to reflect toward the imaging component 110. The imaging component 110 employs one or more of the radiation wavelengths to create one or more images of the packaging material 108. The imaging component 110 sends the images to the computer component 102.

The computer component 102 in one example employs one or more analysis algorithms and the images to determine the package integrity of the packaging material 108. In one example, where the packaging material 108 comprises the normal seal region 512, the analysis algorithms in one example identify one or more dark regions in the images. The dark regions indicate a planar nature of the packaging material 108. In another example, where the packaging material 108 comprises the irregular seal region 514, the analysis algorithms in one example identify one or more bright regions in the images. The bright regions indicate a loss in the planar nature of the packaging material 108. Where the packaging material 108 comprise graphics and/or text, for example in a seal region of the packaging material 108, the imaging component 110 creates one or more images for the computer component 102 that do not show the graphics and/or the text.

Figure 6:
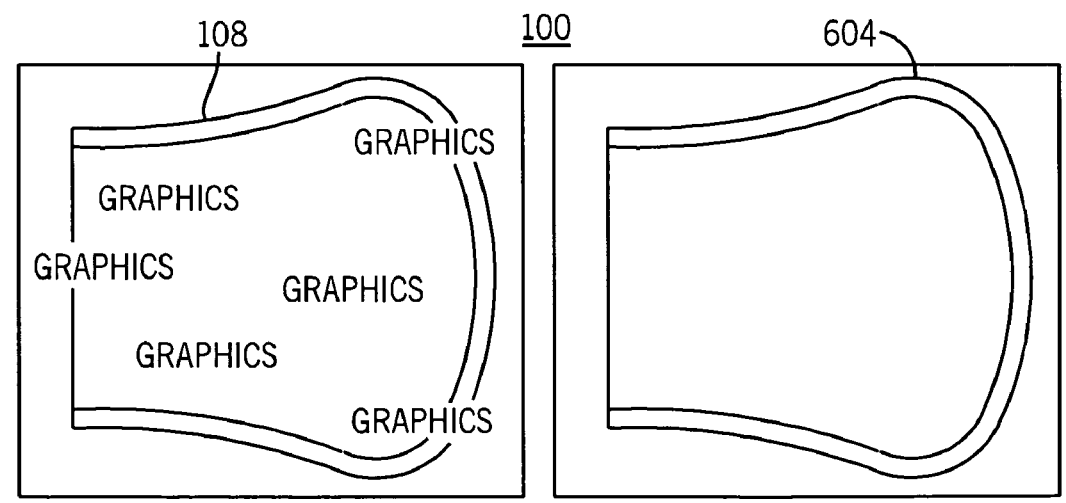
FIG. 6 is a representation of an exemplary implementation of one or more radiation wavelengths illustrating an employment of a packaging material that comprises one or more graphics and/or text that obstruct a passage of a first portion of the radiation wavelengths and allow a passage of a second portion of the radiation wavelength.

Referring to FIGS. 1 and 6, an illustrative description of exemplary operation of the apparatus 100 is now presented, for explanatory purposes. The packaging material 108 in one example comprises one or more graphics and/or text, for example in a seal region of the packing material 108. The computer component 102 employs one or more of the irradiance component 104, the optical components 106, the packaging material 108, and the imaging components 110 to filter out one or more portions of the graphics and/or the text.

The imaging component 110 determines one or more wavelengths of one or more absorption spectrums of the graphics and/or the text of the packaging material 108. In one example, the computer component 102 employs the irradiation component 104 to emit one or more radiation wavelengths other than the wavelengths of the absorption spectrums. In another example, the computer component 102 employs the optical components 106 to filter out the wavelengths of the absorption spectrums from the radiation wavelengths of the irradiation component 104. The imaging component 110 creates one or more images 604 of the packaging material 108. For example, the images do not comprise the graphics and/or the text. The computer component 102 receives the images from the imaging component 110. The computer component 102 in one example employs one or more analysis algorithms and the images to determine the package integrity of the packaging material 108.

Figure 7:
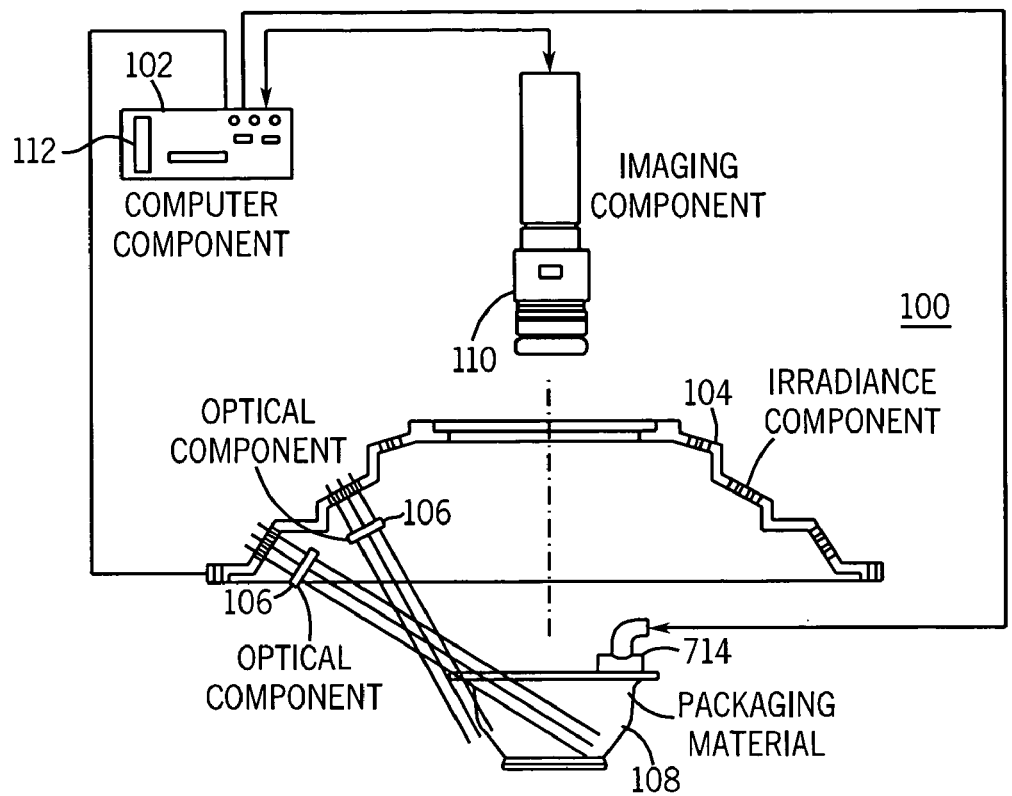
FIG. 7 is a representation of an exemplary implementation of one or more radiation wavelengths illustrating an employment of irradiation components that emit the radiation wavelengths toward a packaging material at one or more angles for employment by an imaging component to create one or more images of the packaging material.

Referring to FIGS. 1 and 7, an illustrative description of exemplary operation of the apparatus 100 is now presented, for explanatory purposes. One or more irradiation components 104 emit one or more radiation wavelengths toward the packaging material 108. The imaging component 110 employs one or more of the radiation wavelengths to create one or more images of the packaging material 108.

The computer component 102 initiates the irradiation components 104. The irradiation components 104 in one example emit one or more radiation wavelengths toward the packaging material 108. For example, the irradiation components 104 emit the radiation wavelengths at incident angles between 20° and 60°. The irradiation components 104 in one example comprise a front lighting arrangement. For example, the front lighting arrangement creates a highly uniform illumination for the packaging material 108. The irradiation components 104 in one example comprise one or more LEDs. For example, the LEDs emit one or more different radiation wavelengths. The different radiation wavelengths comprise structured, semi-structured, or diffuse radiation wavelengths.

The packaging material 108 in one example comprises one or more transparent, translucent, semi-translucent, opaque, semi-specular, and/or specular materials with one or more flanges or seals. Prior to an illumination of the packaging material 108, the irradiation components 104 in one example emit the radiation wavelengths through one or more optical components 106 to filter out one or more of the radiation wavelengths. One or more of the irradiation components 104, the radiation wavelengths, and the optical components 106 in one example allow for the illumination of one or more defects of the packaging material 108.

The computer component in one example employs a materials handling component 712 to create one or more deformations in the packaging material 108 to a make a determination of the defects. For example, the deformations comprise an application of a vacuum or a pressure to the packaging material 108. Where the deformations comprise the application of the vacuum, the materials handling component 712 in one example creates a concavity in the packaging material 108. Where the deformations comprise the application of the pressure, the materials handling component 712 in one example creates a convexity of the packaging materials 108. If the materials handling component 712 does not create the concavity or the convexity upon the application of the vacuum or the pressure, the package integrity of the packaging material 108 in one example is defective. The deformations in one example reveal the seal of the packaging material 108 for the imaging component 110.

The computer component 102 initiates the imaging component 110. The imaging component 110 in one example employs the one or more of the radiation wavelengths to create one or more images of the packaging material 108. The imaging component 110 sends the images to the computer component 102. The computer component 102 in one example employs one or more analysis algorithms and the images to determine the package integrity of the packaging material 108. For example, the analysis algorithms may accept or reject the packaging material 108 based on one or more punctures in the packaging material 108.

Figure 8:
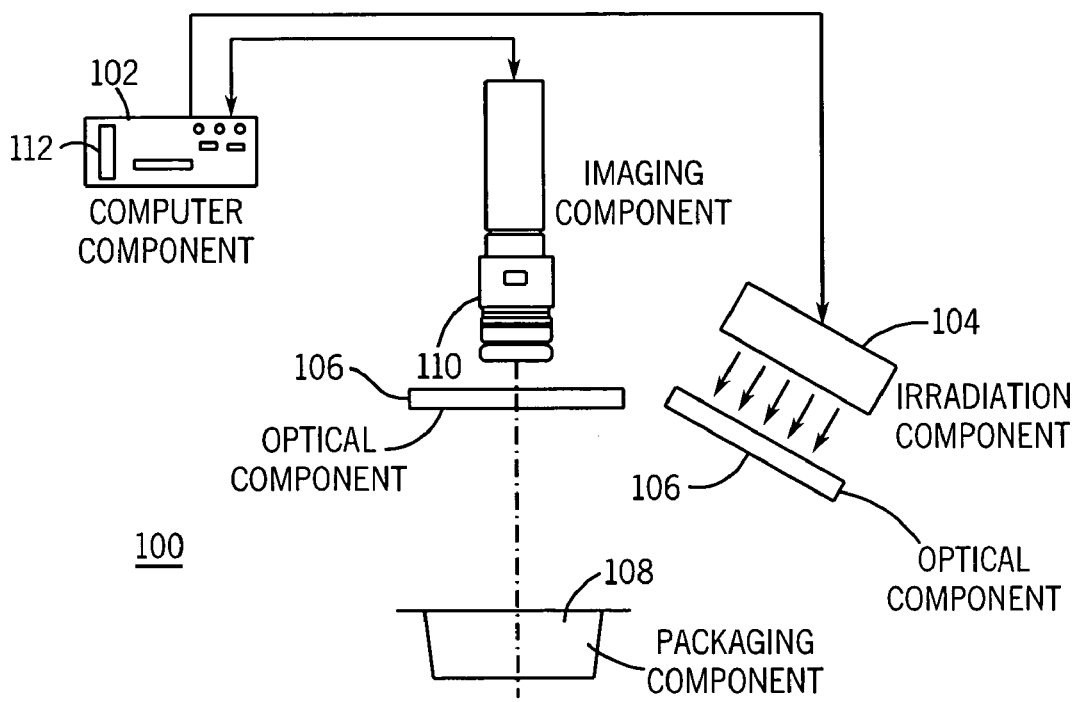
FIG. 8 is a representation of an exemplary implementation of one or more radiation wavelengths that cause one or more portions of a packaging material to fluoresce illustrating an employment of an imaging component that employs one or more of the radiation wavelengths and one or more optical components to collect one or more corresponding fluorescing wavelengths to create one or more images of the packaging material.

Referring to FIGS. 1 and 8, an illustrative description of exemplary operation of the apparatus 100 is now presented, for explanatory purposes. One or more irradiation components 104 emit one or more radiation wavelengths through one or more optical components 106 toward the packaging material 108. The imaging component 110 employs one or more of the radiation wavelengths and the optical components 106 to create one or more images of the packaging material 108.

The computer component 102 initiates the irradiation component 104. The irradiation component 104 in one example emits one or more radiation wavelengths 214 toward the packaging material 108. The irradiation component 104 comprises a fluorescing excitation source. One or more fluorescent radiation wavelengths in one example excite one or more compounds of the packaging material 108 and/or one or more contents of the packaging material 108. A first optical component 106 in one example comprises a band-pass filter. The first optical component 106 filters the radiation wavelengths. For example, the radiation wavelengths that strike the packaging material 108 comprise the fluorescent radiation wavelengths.

Upon bombardment by the fluorescent radiation wavelengths, the compounds in one example emit one or more fluorescing wavelengths. A second optical component 106 comprises a band-pass filter, where the second optical component 106 is different from the first optical component 106. The second optical component 106 in one example allows the fluorescing wavelengths to pass through to the imaging component 110. The imaging component 110 creates one or more images based on the fluorescing wavelengths.

The computer component 102 in one example employs one or more analysis algorithms and the images to determine the package integrity of the packaging material 108. Where, the images in one example comprise one or more bright areas, the package integrity of the packaging material is defective.

The apparatus 100 in one example employs one or more computer-readable signal-bearing media. Examples of a computer-readable signal-bearing medium for the apparatus 100 comprise the recordable data storage medium 112 of the computer component 102. For example, the computer-readable signal-bearing medium for the apparatus 100 comprises one or more of a magnetic, electrical, optical, biological, and atomic data storage medium. In one example, the computer-readable signal-bearing medium comprises a modulated carrier signal transmitted over a network comprising or coupled with the apparatus 100, for instance, one or more of a telephone network, a local area network ("LAN"), the Internet, and a wireless network.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
   a computer component that receives one or more images of one or more packaging materials from one or more imaging components;
   wherein the computer component employs one or more irradiation components to emit one or more radiation wavelengths to the one or more packaging materials, wherein the computer component employs the one or more imaging devices to create the one or more images;
   wherein the one or more packaging materials allow a transmittance of one or more of the one or more radiation wavelengths;
   wherein the computer component employs one or more of the one or more irradiation components to emit the one or more of the one or more radiation wavelengths for the transmittance through one or more of the one or more packaging materials, wherein the one or more of the one or more radiation wavelengths reflect off a carrier of the one or more of the one or more packaging materials to the one or more imaging devices;
   wherein the computer component employs an analysis of the one or more images to make a determination of a package integrity of the one or more packaging materials.

2. The apparatus of claim 1, wherein the computer component employs one or more algorithms to conduct the analysis of one or more of the one or more images to make the determination of the package integrity of the one or more packaging materials.

3. The apparatus of claim 1, wherein the one or more packaging materials comprise one or more seal regions, wherein the package integrity comprises a seal region integrity, wherein the computer component employs the analysis of the one or more images to make the determination of the seal region integrity of the one or more seal regions.

4. The apparatus of claim 1, wherein the one or more packaging materials allow a transmittance of one or more of the one or more radiation wavelengths;
   wherein the computer component employs one or more of the one or more irradiation components to emit the one or more of the one or more radiation wavelengths for a transmittance through one or more of the one or more packaging materials; wherein the one or more of the one or more radiation wavelengths transmit directly through the one or more of the one or more packaging materials to the one or more imaging devices.

5. The apparatus of claim 1, wherein one or more of the one or more packaging materials allow a reflection of the one or more radiation wavelengths;
   wherein the computer component employs one or more of the one or more irradiation components to emit the one or more radiation wavelengths at an incident angle to the one or more of the one or more packaging materials;
   wherein upon the reflection of one or more of the one or more radiation wavelengths at an angle equal to the incident angle, the computer component employs the analysis to identify one or more dark regions in the one or more images, wherein the one or more dark regions indicate the package integrity to the computer component.

6. The apparatus of claim 1, wherein one or more of the one or more packaging materials allow a reflection of the one or more radiation wavelengths;
   wherein the computer component employs one or more of the one or more irradiation components to emit the one or more radiation wavelengths at a low incident angle to the one or more of the one or more packaging materials;
   wherein upon the reflection of one or more of the one or more radiation wavelengths different from the low incident angle, the computer component employs the analysis to identify one or more bright regions in the one or more images, wherein the one or more bright regions indicate the package integrity to the computer component.

7. The apparatus of claim 1, wherein the computer component employs the one or more irradiation components to emit one or more of the one or more radiation wavelengths through one or more optical components.

8. An apparatus, comprising:
   a computer component that receives one or more images of one or more packaging materials from one or more imaging components;
   wherein the computer component employs one or more irradiation components to emit one or more radiation wavelengths to the one or more packaging materials, wherein the computer component employs the one or more imaging devices to create the one or more images;
   wherein the computer component employs the one or more irradiation components to emit one or more of the one or more radiation wavelengths through one or more optical components;
   wherein the computer component employs an analysis of the one or more images to make a determination of a package integrity of the one or more packaging materials;
   wherein one or more of the one or more packaging materials comprise one or more graphics, wherein the computer component employs one or more of the one or more imaging devices to determine one or more absorption spectrums of the one or more graphics;
   wherein the computer component employs the one or more of the one or more irradiation components to emit the one or more of the one or more radiation wavelengths to the one or more of the one or more packaging materials, wherein the computer component employs the one or more optical components to filter out the one or more absorption spectrums from the one or more of the one or more radiation wavelengths.

9. The apparatus of claim 7, wherein the computer component employs the one or more of the one or more irradiation components and the one or more optical components to create the one or more of the one or more radiation wavelengths, wherein the one or more of the one or more radiation wavelengths contact one or more of the one or more packaging materials.

10. An apparatus, comprising:
a computer component that receives one or more images of one or more packaging materials from one or more imaging components;
wherein the computer component employs one or more irradiation components to emit one or more radiation wavelengths to the one or more packaging materials, wherein the computer component employs the one or more imaging devices to create the one or more images;
wherein the computer component employs the one or more irradiation components to emit one or more of the one or more radiation wavelengths through one or more optical components;
wherein the computer component employs an analysis of the one or more images to make a determination of a package integrity of the one or more packaging materials;
wherein the one or more of the one or more irradiation components comprise one or more fluorescing excitation sources, wherein the one or more optical components comprise a first band-pass filters, wherein the first band-pass filter allows the one or more of the one or more radiation wavelengths of the one or more fluorescing excitation sources to pass through to one or more of the one or more packaging materials;
wherein one or more compounds within the one or more of the one or more packaging materials react to the one or more of the one or more radiation wavelengths of the one or more fluorescing excitation sources, wherein the one or more compounds emit one or more fluorescing wavelengths;
wherein the one or more optical components comprise a second band-pass filters, wherein the second band-pass filter allows the one or more fluorescing wavelengths to pass through to the one or more imaging devices.

11. The apparatus of claim 1, wherein the computer component employs one or more material handling components to cause one or more deformations in one or more of the one or more packaging materials;
wherein the computer component receives one or more images of the one or more deformations from the one or more imaging components;
wherein the computer component employs an analysis of the one or more deformations to make a determination of the package integrity of the one or more of the one or more packaging materials.

12. The apparatus of claim 1, wherein the computer component receives the one or more images of the one or more packaging materials from the one or more imaging components to perform an automated inspection of the package integrity of the one or more packaging materials.

13. A method, comprising the steps of:
employing one or more irradiation components to emit one or more radiation wavelengths to one or more packaging materials, wherein the one or more packaging materials allow a transmittance of one or more of the one or more radiation wavelengths, wherein the one or more imaging devices create the one or more images of the one or more packaging materials;
receiving one or more images of the one or more packaging materials from one or more imaging components; and
employing one or more analysis algorithms on the one or more images to make a determination of a package integrity of the one or more packaging materials;
wherein the step of receiving the one or more images of the one or more packaging materials from the one or more imaging components comprises the steps of:
employing the one or more irradiation components to emit the one or more of the one or more radiation wavelengths for the transmittance through the one or more packaging materials; and
receiving the one or more images from the one or more imaging devices upon a reflection of the one or more of the one or more radiation wavelengths off a carrier of the one or more packaging materials to the one or more imaging devices.

14. The method of claim 13, wherein the one or more packaging materials allow a transmittance of one or more of the one or more radiation wavelengths, wherein the one or more imaging devices create the one or more images of the one or more packaging materials, wherein the step of receiving the one or more images of the one or more packaging materials from the one or more imaging components comprises the steps of:
employing the one or more irradiation components to emit the one or more of the one or more radiation wavelengths for the transmittance through the one or more packaging materials; and
receiving the one or more images from the one or more imaging devices images upon the transmittance of the one or more of the one or more radiation wavelengths through the one or more packaging materials to the one or more imaging devices.

15. The method of claim 13, wherein the one or more packaging materials allow a reflection of the one or more radiation wavelengths, wherein the step of employing the one or more analysis algorithms on the one or more images to make the determination of the package integrity of the one or more packaging materials comprises the steps of:
employing the one or more irradiation components to emit the one or more radiation wavelengths at an incident angle to the one or more packaging components;
receiving the one or more images from the one or more imaging devices upon the reflection of one or more of the one or more radiation wavelengths at an angle equal to the incident angle;
employing the one or more analysis algorithms to identify one or more dark regions of the one or more images; and
employing the one or more dark regions of the one or more images to make the determination of the package integrity to the computer component.

16. The method of claim 13, wherein the one or more packaging materials allow a reflection of the one or more radiation wavelengths, wherein the step of employing the one or more analysis algorithms on the one or more images to make the determination of the package integrity of the one or more packaging materials comprises the steps of:
employing one or more of the one or more irradiation components to emit the one or more radiation wavelengths at a low incident angle to the one or more packaging components;

receiving the one or more images from the one or more imaging devices upon the reflection of one or more of the one or more radiation wavelengths at an angle different from the incident angle; and employing the one or more analysis algorithms to identify one or more bright regions of the one or more images;

employing the one or more bright regions of the one or more images to make the determination of the package integrity to the computer component.

17. A method, comprising the steps of:

employing one or more irradiation components to emit one or more radiation wavelengths to one or more packaging materials, wherein the one or more packaging materials comprise one or more graphics;

receiving one or more images of the one or more packaging materials from one or more imaging components; and employing one or more analysis algorithms on the one or more images to make a determination of a package integrity of the one or more packaging materials;

wherein the step of employing the one or more irradiation components to emit the one or more radiation wavelengths to the one or more packaging materials comprises the steps of:

employing the one or more imaging devices to determine one or more absorption spectrums of the one or more graphics; and employing the one or more irradiation components to emit one or more of the one or more radiation wavelengths through one or more optical components, wherein the one or more optical components filter out the one or more absorption spectrums from the one or more of the one or more radiation wavelengths.

18. A method, comprising the steps of:

employing one or more irradiation components to emit one or more radiation wavelengths to one or more packaging materials, wherein the one or more irradiation components comprise one or more fluorescing excitation sources;

receiving one or more images of the one or more packaging materials from one or more imaging components; and employing one or more analysis algorithms on the one or more images to make a determination of a package integrity of the one or more packaging materials;

wherein the step of employing the one or more irradiation components to emit the one or more radiation wavelengths to the one or more packaging materials comprises the steps of:

employing a first optical component to allow a transmittance of one or more of the one or more radiation wavelengths from the one or more fluorescing excitation sources through the one or more packaging materials; and employing a second optical component to allow one or more fluorescing wavelengths emitted by the one or more packaging materials to pass through to the one or more imaging devices.

19. An article, comprising:

one or more computer-readable signal-bearing media;

means in the one or more media for employing one or more irradiation components to emit one or more radiation wavelengths to one or more packaging materials, wherein the one or more packaging materials comprise one or more graphics;

means in the one or more media for receiving one or more images of the one or more packaging materials from one or more imaging components; and means in the one or more media for employing one or more analysis algorithms on the one or more images to make a determination of a package integrity of the one or more packaging materials;

wherein the means in the one or more media for employing the one or more irradiation components to emit the one or more radiation wavelengths to the one or more packaging materials comprises:

means in the one or more media for employing the one or more imaging devices to determine one or more absorption spectrums of the one or more graphics; and means in the one or more media for employing the one or more irradiation components to emit one or more of the one or more radiation wavelengths through one or more optical components, wherein the one or more optical components filter out the one or more absorption spectrums from the one or more of the one or more radiation wavelengths.

* * * * *